(12) United States Patent
Heddi et al.

(10) Patent No.: US 11,642,073 B2
(45) Date of Patent: May 9, 2023

(54) SYSTEM AND METHOD FOR CALCULATION OF AN INDEX OF BRAIN ACTIVITY

(71) Applicants: BIOSERENITY, Paris (FR); ICM (INSTITUT DU CERVEAU ET DE LA MOELLE ÉPINIÈRE), Paris (FR); APHP (ASSISTANCE PUBLIQUE—HÔPITAUX DE PARIS), Paris (FR); SORBONNE UNIVERSITE, Paris (FR); CENTRE NATIONAL DE LA RECHERCHE SCIENTIFIQUE, Paris (FR); INSERM (INSTITUT NATIONAL DE LA SANTÉ ET DE LA RECHERCHE MÉDICALE), Paris (FR)

(72) Inventors: Mohcine Heddi, Paris (FR); Michel Le Van Quyen, Paris (FR); Jean-Eudes Le Douget, Paris (FR)

(73) Assignees: BIOSERENTIY, Paris (FR); ICM (INSTITUT DU CERVEAU ET DE LA MOELLE ÈPINIÈRE, Paris (FR); APHP (ASSISTANCE PUBLIQUE—HÔPITAUX DE PARIS), Paris (FR); SORBONNE UNIVERSITE, Paris (FR); CENTRE NATIONAL DE LA RECHERCHE SCIENTTIFIQUE, Paris (FR); INSERM (INSTITUT CENTRE NATIONAL DE LA RECHERCHE SCIENTTIFIQUE NATIONAI DF TA SANTÉ ET DF TA RECHERCHE MÉDICALE, Paris (FR)

( * ) Notice: Subject to any disclaimer, the term of this patent is extended or adjusted under 35 U.S.C. 154(b) by 277 days.

(21) Appl. No.: 16/954,749

(22) PCT Filed: Dec. 21, 2018

(86) PCT No.: PCT/EP2018/086730
§ 371 (c)(1),
(2) Date: Jun. 17, 2020

(87) PCT Pub. No.: WO2019/122396
PCT Pub. Date: Jun. 27, 2019

(65) Prior Publication Data
US 2021/0085236 A1  Mar. 25, 2021

(30) Foreign Application Priority Data
Dec. 22, 2017 (EP) .................................... 17306917

(51) Int. Cl.
| G08B 21/04 | (2006.01) |
| A61B 5/00 | (2006.01) |
| G16H 50/30 | (2018.01) |
| G16H 50/70 | (2018.01) |

(52) U.S. Cl.
CPC .......... *A61B 5/4094* (2013.01); *A61B 5/7267* (2013.01); *G16H 50/30* (2018.01); *G16H 50/70* (2018.01)

(58) Field of Classification Search
USPC ......... 340/539.12, 539.24, 4.1, 539.3, 568.1, 340/619, 636.15, 4.11
See application file for complete search history.

(56) References Cited

U.S. PATENT DOCUMENTS

| 5,119,816 A | * | 6/1992 | Gevins | ................... | G01R 33/28 |
| | | | | | 600/386 |
| 2002/0062089 A1 | * | 5/2002 | Johnson, Jr. | ........... | A61B 5/377 |
| | | | | | 600/544 |

(Continued)

FOREIGN PATENT DOCUMENTS

GB  2 404 251 A  1/2005

OTHER PUBLICATIONS

International Search Report and Written Opinion dated Mar. 21, 2019 in corresponding application No. PCT/EP2018/086730; 12 pgs.

(Continued)

*Primary Examiner* — Daniel Previl
(74) *Attorney, Agent, or Firm* — Lee & Hayes, P.C.

(57) ABSTRACT

A system for calculating an indicator associated to a brain activity of a subject, the system including an acquisition module configured to acquire at least an epoch of electro- (Continued)

encephalographic signal of a subject from a plurality of electrodes and a data processing module configured to carry out the steps of: calculating an average vector ($V_A$) using as input of an autoencoder neural network (aNN) an electro-encephalographic signals (ES) of a subject acquired from a plurality of electrodes; detecting (DET) the presence of at least a predefined pattern in the consecutive average values of the average vector ($V_A$); and generating an indicator of brain activity (Idx) of the subject when detecting the predefined pattern.

21 Claims, 3 Drawing Sheets

(56) References Cited

U.S. PATENT DOCUMENTS

| | | | | |
|---|---|---|---|---|
| 2010/0042011 | A1* | 2/2010 | Doidge | G06T 17/10 600/544 |
| 2012/0101401 | A1* | 4/2012 | Faul | A61B 5/369 600/544 |
| 2012/0245481 | A1* | 9/2012 | Blanco | A61B 5/7264 600/544 |
| 2014/0121554 | A1* | 5/2014 | Sarma | A61B 5/4094 600/544 |
| 2017/0087301 | A1* | 3/2017 | Wu | A61B 5/369 |
| 2017/0143229 | A1* | 5/2017 | Weffers-Albu | A61B 5/4519 |
| 2021/0169417 | A1* | 6/2021 | Burton | A61B 5/4857 |

OTHER PUBLICATIONS

Thodoroff, Pierre, Joelle Pineau, and Andrew Lim. "Learning Robust Features using Deep Learning for Automatic Seizure Detection" Machine Learning for Healthcare Conference, 2016; 12 pgs.
Berg et al., "Revised terminology and concepts for organization of seizures and epilepsies: Report of the ILAE Commission on Classification and Terminology, 2005-2009", Epilepsia, 51(4):676-685, 2020, 10 pgs.

* cited by examiner

SYSTEM AND METHOD FOR CALCULATION OF AN INDEX OF BRAIN ACTIVITY

FIELD

The present invention relates to a system and a method for the analysis of an electroencephalogram of a subject. In particular, the invention relates to a system and a method for the identification of pathological brain activity in a subject using a classification method.

BACKGROUND

Electroencephalography, consisting in recording brain electrical activity with electrodes placed on the surface of a subject's scalp, is a fundamental tool for diagnosis and research of neurological disorders such as epilepsy.

Traditionally, clinical review of the scalp electroencephalogram relies on visual evaluation of the morphology and spatial distribution of recorded waveform patterns in multiple channels, which is often a time consuming and inefficient procedure. The present invention proposes a method capable of automatically detecting pathological brain activity such as epileptic seizures as well as other neurophysiological phenomena.

The problem of automatic seizure detection has been extensively studied. Up to date most work uses expert hand-crafted features characteristic of seizure manifestations in EEG.

However, epileptic seizures are highly non-stationary phenomena and seizure manifestations in EEG are extremely variable both within a patient over time, and between different patients (Panayiotopoulos CP. "*A clinical guide to epileptic syndromes and their treatment.*" Chapter 6. Springer, 2010). In this context had arose the need to improve the generalization error in automated seizure detection both intra- and inter-patient.

Thodoroff et al. have proposed in their publication (Thodoroff, Pierre, Joelle Pineau, and Andrew Lim. "*Learning Robust Features using Deep Learning for Automatic Seizure Detection.*" Machine Learning for Healthcare Conference, 2016) a method to overcome said technical issues. Thodoroff et al. discloses a method using deep learning in a supervised learning framework to automatically learn more robust features. Indeed, features designed by deep learning models have proven to be more robust than hand-crafted features in various field. More precisely, Thodoroff et al. discloses the implementation of a recurrent convolutional neural network able to learn a general spatially invariant representation of a seizure. This method allows to detect whether a 30 second segment of electroencephalographic signal contains a seizure or not for a patient-specific and cross-patient detection. However, Thodoroff et al. generates handwritten features. Furthermore, the occurrence of two distinct seizures in a time period equal or shorted than 30 seconds will be wrongly associated to a unique seizure, limiting the intrinsic sensitivity of the method disclosed by Thodoroff et al.

There is therefore a need to develop a method for the analysis of electroencephalographic signal and the detection of brain activity as seizures providing a higher temporal resolution and intrinsic sensitivity.

SUMMARY

To this end, the invention relates to a system for calculating an indicator associated to a brain activity of a subject, the system comprising:

- acquisition module for acquiring at least an epoch of electroencephalographic signal of a subject from a plurality of electrodes;
- a data module comprising means for carrying out the steps:
  - calculating an average vector according to the following steps:
    - receiving at least an epoch of electroencephalographic signals of a subject acquired from a plurality of electrodes;
    - generating an input matrix (n×m) of said electroencephalographic signals, for an auto-encoder neural network, said input matrix having the n dimension equal to N, wherein N is the number of channels of the electroencephalographic recording;
    - generating a reconstructed output matrix using the auto-encoder;
    - generating a loss values vector by linear combination of the input matrix and output matrix, wherein each element of the loss value vector is associated to a channel;
    - calculating the average value of the elements of the loss values vector; said calculating step being repeated multiple times to generate an average vector comprising the average values obtained for each consecutive electroencephalographic epoch;
  - detecting the presence of at least a predefined pattern in the consecutive average values of the average vector; and
  - generating an indicator of brain activity of the subject when detecting the predefined pattern.

The system of the present invention advantageously makes it possible to acquire and analyze electroencephalographic signal in order to detect at least one specific brain activity, such as seizures, with a high temporal resolution and high intrinsic sensitivity.

In one embodiment, the autoencoder implemented in the data module is trained with a training dataset comprising a plurality of predefined electroencephalographic signals over a predefined time period.

In one embodiment, the autoencoder implemented in the data module comprises at least two hidden layers of neurons In one embodiment, the data processing module is further configured to carry out a step of binary classifying the elements of the average vector according to a predefined threshold.

In one embodiment, in the data processing module, each average value of the elements of the loss values vector is calculated with a harmonic mean.

In one embodiment, in the data processing module, the predefined pattern is configured to detect two consecutive average values of the average vector comprised in a predefined range of values.

In one embodiment, the electroencephalographic signal is acquired by the acquisition module at a sampling rate of at least 256 Hz.

In one embodiment, in the data processing module, the m dimension of the input matrix is defined according to the sampling rate and the epoch time window.

In one embodiment, in the data processing module, the predefined threshold is a value below which 98 percent of the elements of the average vector falls.

In one embodiment, the system further comprises an output generator for reporting the indicator of the brain activity.

The invention also relates to a method for calculating an indicator associated to a brain activity of a subject, said method comprising the following steps:

calculating an average vector according to the following steps:

receiving at least an epoch of electroencephalographic signals of a subject acquired from a plurality of electrodes;

generating an input matrix (n×m) of said electroencephalographic signals, for an auto-encoder neural network, said input matrix having the n dimension equal to N, wherein N is the number of channels of the electroencephalographic recording;

generating a reconstructed output matrix using the auto-encoder;

generating a loss values vector by linear combination of the input matrix and output matrix, wherein each element of the loss value vector is associated to a channel;

calculating the average value of the elements of the loss values vector; said calculating step being repeated multiple times to generate an average vector comprising the average values obtained for each consecutive electroencephalographic epoch;

detecting the presence of at least a predefined pattern in the consecutive average values of the average vector; and generating an indicator of brain activity of the subject when detecting the predefined pattern.

The method of the present invention advantageously makes it possible to analyze electroencephalographic signal and therefore the detection of specific brain activity, such as seizures, with a higher temporal resolution and an intrinsic sensitivity.

Furthermore, the implementation of an autoencoder allows the use of unsupervised learning which does not need an external teaching signal (i.e. training dataset without classifying the signals).

In one embodiment, the autoencoder is trained with a training dataset comprising a plurality of predefined electroencephalographic signals over a predefined time period.

In one embodiment, the auto-encoder comprises at least two hidden layers of neurons.

In one embodiment, the method further comprises a step of binary classifying the elements of the average vector according to a predefined threshold.

This approach as the advantage of removing the noisy events that have been misclassified as pathological brain activity.

In one embodiment, each average value of the elements of the loss values vector is calculated with a harmonic mean.

In one embodiment, the predefined pattern is configured to detect two consecutive average values of the average vector comprised in a predefined range of values.

In one embodiment, the electroencephalographic signal is acquired at a sampling rate of at least 256 Hz.

In one embodiment, the m dimension of the input matrix ($M_{in}$) is defined according to the sampling rate and the epoch time window.

In one embodiment, the predefined threshold is a value below which 98 percent of the elements of the average vector falls.

The invention also relates to a computer program product for calculating an indicator associated to a brain activity of a subject, the computer program product comprising instructions which, when the program is executed by a computer, cause the computer to carry out the steps of the method of the present invention, according to any one of the embodiments described hereabove.

The invention also relates to a computer-readable storage medium comprising instructions which, when the program is executed by a computer, cause the computer to carry out the steps of the method of the present invention, according to any one of the embodiments described hereabove.

In the present invention, the following terms have the following meanings:

"As" used herein the singular forms "a", "an", and "the" include plural reference unless the context clearly dictates otherwise.

The term "about" is used herein to mean approximately, roughly, around, or in the region of. When the term "about" is used in conjunction with a numerical range, it modifies that range by extending the boundaries above and below the numerical values set forth. In general, the term "about" is used herein to modify a numerical value above and below the stated value by a variance of 20 percent, preferably of 5 percent.

"Abnormal brain activity" refers to brain electrical activity that is present in brain disorders and that is different from physiological activity, such as for example interictal epileptiform discharges and electrographic seizures, known to be characteristic for epilepsy.

"Electrode" refers to a conductor used to establish electrical contact with a nonmetallic part of a circuit, preferably a subject body. For instance, EEG electrodes are small metal discs usually made of stainless steel, tin, gold, silver covered with a silver chloride coating; there are placed on the scalp at specific positions.

"Electroencephalogram" refers to the record of the electrical activity of the brain of a subject.

"Epoch" refers to a determined period of the electroencephalographic signal that is analyzed independently. Epochs are not overlapping.

"Physiological brain activity" refers to the normal electrical activity of the brain such as for examples the occipital alpha rhythm, sleep spindles, K-complexes and slow waves of sleep.

"Subject" refers to a mammal, preferably a human. In the sense of the present invention, a subject may be a patient, i.e. a person receiving medical attention, undergoing or having underwent a medical treatment, or monitored for the development of a disease.

"Seizure" refers to a transient occurrence of signs and/or symptoms due to abnormal, excessive and synchronous neuronal activity in the brain.

DETAILED DESCRIPTION

The following detailed description will be better understood when read in conjunction with the drawings. For the purpose of illustrating, the system is shown in the preferred embodiments. It should be understood, however that the application is not limited to the precise arrangements, structures, features, embodiments, and aspect shown. The drawings are not drawn to scale and are not intended to limit the scope of the claims to the embodiments depicted. Accordingly, it should be understood that where features mentioned in the appended claims are followed by reference signs, such signs are included solely for the purpose of enhancing the intelligibility of the claims and are in no way limiting on the scope of the claims.

This invention relates to a method for calculating an indicator associated to a brain activity in a subject. According to one embodiment, said method is computer implemented.

According to one embodiment, the method of the present invention comprises the steps of:
  a) calculating an average vector $V_A$ from an electroencephalographic signal ES;
  b) detecting DET the presence of at least a predefined pattern in the consecutive average values of the average vector $V_A$; and
  c) generating an indicator of brain activity Idx of the subject when detecting the predefined pattern.

Figure 1:
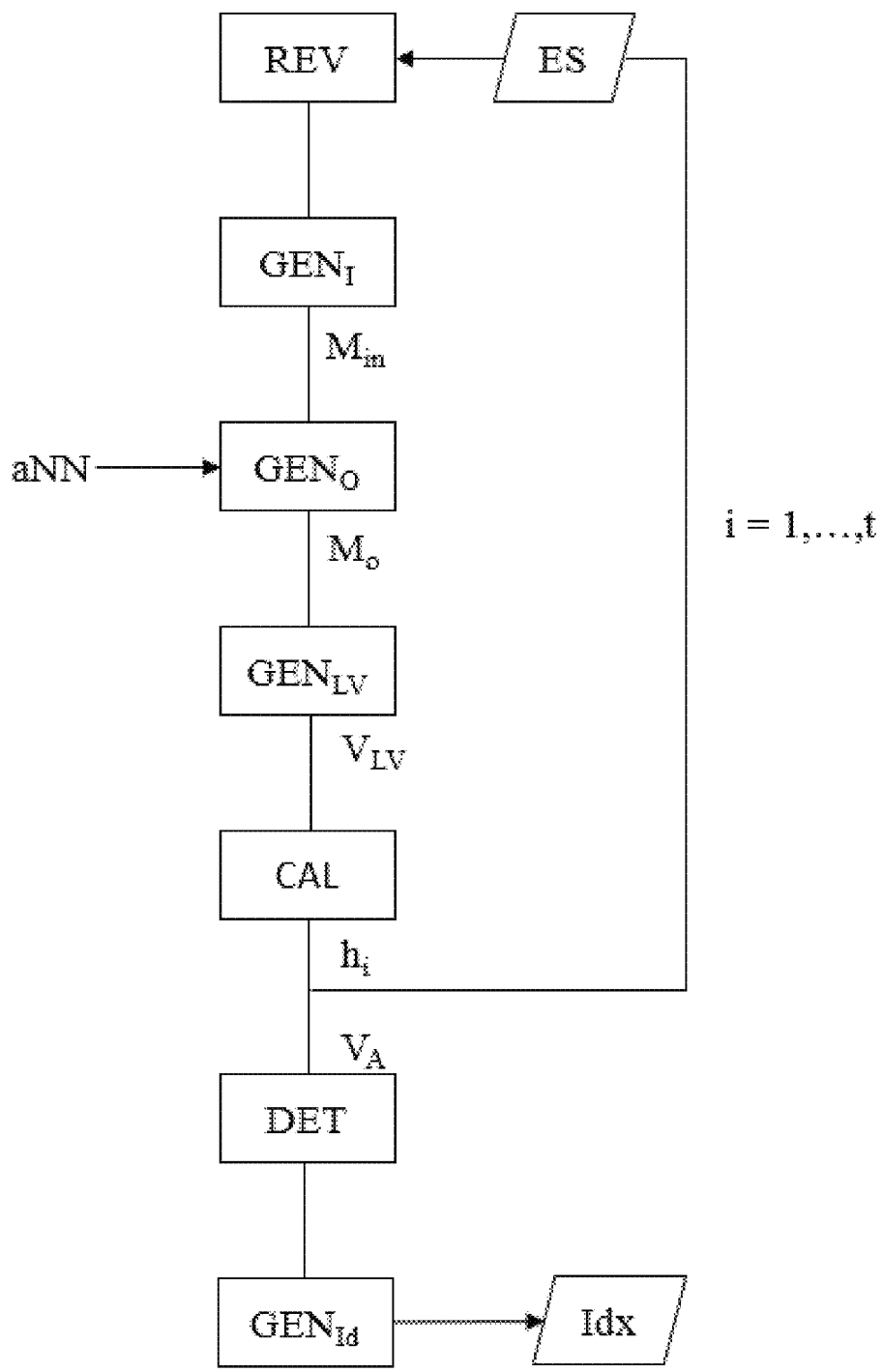
FIG. 1 shows a flow chart schematically illustrating one non-limiting example of a method for calculating an indicator of brain activity.

The schematic flowchart illustrating this embodiment are show in FIG. 1.

The schematic flowchart diagrams in the Figures illustrate the functionality and operation of possible implementations of methods and computer program products according to various embodiments of the present invention. In this regard, each block in the schematic flowchart diagrams may represent a module, segment, or portion of code, which comprises one or more executable instructions of the program code for implementing the specified logical function(s).

It should also be noted that, in some alternative implementations, the functions noted in the block may occur out of the order noted in the Figures. For example, two blocks shown in succession may, in fact, be executed substantially concurrently, or the blocks may sometimes be executed in the reverse order, depending upon the functionality involved. Other steps and methods may be conceived that are equivalent in function, logic, or effect to one or more blocks, or portions thereof, of the illustrated Figures.

Although various arrow types and line types may be employed in the flowchart, they are understood not to limit the scope of the corresponding embodiments. Indeed, some arrows or other connectors may be used to indicate only the logical flow of the depicted embodiment. For instance, an arrow may indicate a waiting or monitoring period of unspecified duration between enumerated steps of the depicted embodiment. It will also be noted that each block and combinations of blocks flowchart diagrams, can be implemented by special purpose hardware-based systems that perform the specified functions or acts, or combinations of special purpose hardware and computer readable program code.

According to one embodiment, the present invention comprises a preliminary step of receiving REV an electroencephalographic signal ES of a subject from multiple channels and as a function of time.

According to one embodiment, the electroencephalographic signal received is recorded from a plurality of electrodes, positioned onto predetermined areas of the scalp of the subject in order to obtain a multi-channel electroencephalographic signal. According to one embodiment, the electroencephalographic signals are acquired by at least 4, 8, 10, 15, 16, 17, 18, 19, 20, 21, 32, 64, 128 or 256 electrodes. According to one embodiment, the electrodes are placed on the scalp according to the 10-10 or 10-20 system, dense-array positioning or any other electrodes positioning known by the man skilled in the art. The electrodes montage may be unipolar or bipolar. In a preferred embodiment, the electrodes are placed accordingly to the 10-20 system in a bipolar montage with locations FP1-F7, F7-T7, T7-P7, P7-O1, FP1-F3, F3-C3, C3-P3, P3-O1, FP2-F4, F4-C4, C4-P4, P4-O2, FP2-F8, F8-T8, T8-P8, P8-O2, FZ-CZ, CZ-PZ, T7-FT9, FT9-FT10 and FT10-T8. In one embodiment, the plurality of electrodes are dry electrodes or semi-dry electrodes. Electrode material may be a metal such as stainless steel or copper, such as inert metals, like, gold, silver (silver/silver chloride), tin and the like. The electrodes may be flexible, preshaped or rigid, and in any shape, for example, a sheet, rectangular, circular, or such other shape conducive to make contact with the wearer's skin. In a preferred embodiment, the electrodes are textile electrodes. In said embodiment, various types of suitable headsets or electrode systems are available for acquiring such neural signals. Examples includes, but are not limited to: Epoc headset commercially available from Emotiv, Waveguard headset commercially available from ANT Neuro, Versus headset commercially available from SenseLabs, DSI 6 headset commercially available from Wearable sensing, Xpress system commercially available from BrainProducts, Mobita system commercially available from TMSi, Porti32 system commercially available from TMSi, ActiChamp system commercially available from BrainProducts and Geodesic system commercially available from EGI.

The electroencephalographic signals received may be obtained with a standard recording module with sampling frequency of at least 24 Hz, 32 Hz, 64 Hz, 128 Hz or any other sampling frequency known by the man skilled in the art. In a preferred embodiment, the sampling rate is of at least 256 Hz.

According to another embodiment, the electroencephalographic signal is recorded during a predefined period of time and stored in a storage medium. According to another embodiment, the electroencephalographic signal is received from a database, such as for example a medical database.

According to one embodiment, the electroencephalographic signals are further pre-processed in order to remove or reject artefact. According to one embodiment, the electroencephalographic signals from individual scalp electrodes are digitally filtered with at least one filter chosen from group: low-frequency reject filter, high-frequency reject filter, bandpass filter, band stop filter. In a preferential embodiment, electroencephalographic signals may be filtered using first-order Butterworth band-pass filter and a third-order Butterworth notch filter; a skilled artisan would be able to select a suitable range of frequencies to reject. In a preferred embodiment, the signal is not pre-processed in order to remove or reject artefacts.

According to one embodiment, the continuous electroencephalographic signals received in the processor are segmented into epochs having a time window ranging from 1 to 30 seconds. An epoch may have a time duration comprised between 1 and 10 seconds or 11 to 30 seconds, preferably an epoch may have a duration of 2 seconds. The choice of shorter time windows allows to analyses more accurately the signal.

According to one embodiment, the method of the present invention uses a classification model to analyze the electroencephalographic signals. In one embodiment, the model that is created can be formed using unsupervised learning methods. Unsupervised learning uses a data driven approach that is suitable for neural decoding without any need for an external teaching signal. Unsupervised learning can attempt to learn clustering based on similarities in a training dataset, without pre-classifying the signals from which the training dataset was derived.

Figure 2:
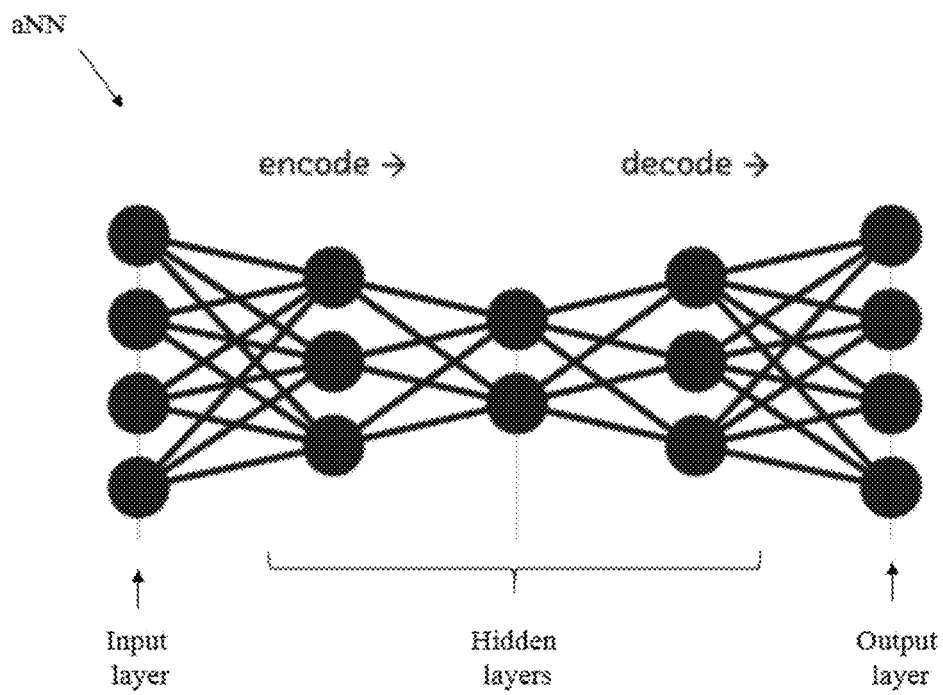
FIG. 2 shows a schematic representation of an auto-encoder neural network aNN according to one of the embodiment of the present invention.

In a preferred embodiment, the classification model created is a discriminative regular autoencoder. An autoencoder neural network is trained using backpropagation, in order to set up the target values to be equal to the inputs (i.e. $y^{(i)}=x^{(i)}$. Specifically, autoencoders sequentially deconstruct (i.e. encode) input data into hidden representations, then use these representations to sequentially reconstruct (i.e. decode) outputs that resemble the originals. According to one embodiment, the autoencoder is a feedforward, non-recurrent neural network having an input vector and an output layer and wherein the output layer have an equal number of nodes as the input vector, due to the purpose of reconstructing its own inputs, as shown in FIG. 2. According to one embodiment, the input layer and the output layer are connected by at least two hidden layers. According to one embodiment, the number of hidden layers ranges from 2 to 10. In a preferred embodiment, the number of hidden layer is 6.

According to one embodiment, the autoencoder is trained with one of the many variants of backpropagation such as conjugate gradient method, steepest descent, etc. According to one embodiment, the autoencoder is trained with a training dataset comprising a plurality of predefined electroencephalographic signals. According to one embodiment, the electroencephalographic signals comprised in the training dataset are scalp electroencephalographic signals acquired from subjects of different gender and age.

According to one embodiment, the electroencephalographic signals of the training dataset do not present signal anomalies other than artefacts or noise. In the present description, the terms "signal anomalies" refers to those patters in an electroencephalographic signal that arises from a pathological behavior of a subject brain. The exclusion from the training dataset of electroencephalographic signals presenting abnormal brain activity, (i.e. due to a pathology of the subject) implies that the autoencoder is trained solely on electroencephalographic signal deriving from physiological brain activity and therefore the autoencoder is only capable of encoding physiological brain activity signal. As consequence, the autoencoder will provide an output different from the input whenever the input comprises an electroencephalographic signal with abnormal brain activity.

According to one embodiment, the training of the autoencoder is performed over a predefined time period.

According to one embodiment, the at least one epoch of electroencephalographic signals ES received in the processor is entered as input to the autoencoder. According to this embodiment, the method of the present invention comprises a step of generating $GEN_I$ an input matrix $M_{in}$ with dimensions (n×m) of said electroencephalographic signals, wherein the n dimension is equal to N, with N number of channels of the electroencephalographic recording. According to one embodiment, m dimension is defined according to the sampling frequency and the duration of the electroencephalographic signal epoch, for example for a sampling frequency of 256 Hz and an epoch of 2 seconds the m dimension is equal to 512. In another example, m dimension may be of 384 when the sampling frequency is equal to 128 Hz and the epoch duration is equal to 3 seconds.

According to one embodiment, the method comprises a step $GEN_O$ of generating a reconstructed output matrix $M_o$ using the autoencoder aNN according to the embodiments hereabove. According to one embodiment, the output matrix $M_o$ generated has dimension (n×m) as the input matrix $M_{in}$. As previously mentioned, the output matrix $M_o$ generated should be substantially equal to the input matrix $M_{in}$ if the electroencephalographic signals in $M_{in}$ do not present any signal anomalies. Inversely, since the autoencoder aNN is trained on a training dataset absent from pathological brain activities, the autoencoder aNN is unable to reconstruct output matrix $M_o$ substantially equal to the input matrix $M_{in}$ if the electroencephalographic signals in $M_{in}$ presents pathological brain activities. Therefore, an evaluation of the differences between the input matrix $M_{in}$ and the output matrix $M_o$ generated provides an information concerning the presence or not of pathological brain activities in the electroencephalographic epoch under analysis.

Figure 3:
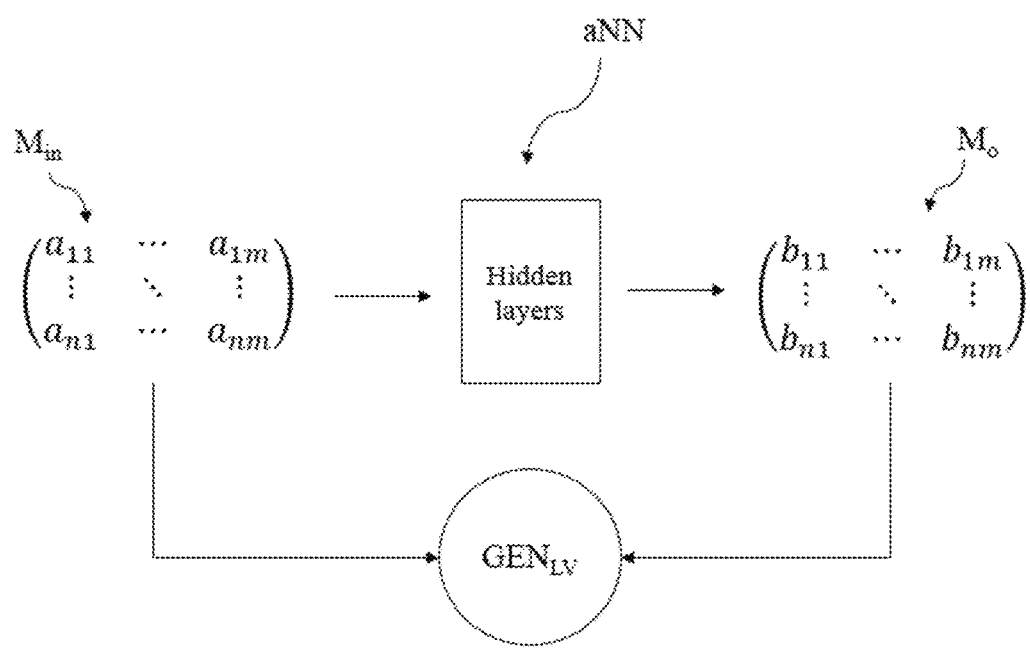
FIG. 3 shows a schematic representation of the method's step $GEN_{LV}$ consisting in generating a loss values vector $V_{LV}$ by linear combination of the input matrix $M_{in}$ and output matrix $M_o$ according to one of the embodiment of the present invention.

According to one embodiment, the method of the present invention comprises a step $GEN_{LV}$ consisting in generating a loss values vector $V_{LV}$ by linear combination of the input matrix $M_{in}$ and output matrix $M_o$, as shown in FIG. 3, wherein each element of the loss value vector $V_{LV}$ is associated to a channel. According to one embodiment, the linear combination of the input matrix $M_{in}$ and output matrix $M_o$ is a difference between those two matrices or any other operation between metrices known by the man skill in the art that would provide an estimation of the discrepancy between them. The loss values vector $V_{LV}$ may have one dimension equal to the number of channels acquired N and the other equal to one, so that the $i^{th}$ component of the loss values vector $V_{LV}$ represents the discrepancy between the input electroencephalographic signal and output electroencephalographic signal for the $i^{th}$ channel, for one epoch.

According to one embodiment, the method of the present invention further comprises a step CAL of calculating the average value $h_i$ of the elements of the loss values vector $V_{LV}$. By means of non-limiting example, the average value $h_i$ may be obtained with an arithmetic mean, weighted arithmetic mean, a geometric mean or the like. In a preferred embodiment, each average value $h_i$ of the elements of the loss values vector is calculated with a harmonic mean.

According to one embodiment, the multiple steps described hereabove which leads to the calculation of the average value $h_i$ are repeated multiple times over consecutive electroencephalographic signal epochs to generate an average vector $V_A$ comprising the average values obtained for each consecutive electroencephalographic epoch. Therefore, the length of average vector $V_A$ depends on the number of epochs in which the electroencephalogram to analyze have been segmented.

According to one embodiment, the step of calculating an average vector $V_A$ is followed by the step of detecting DET the presence of at least a predefined pattern in the consecutive average values of the average vector $V_A$. The presence of at least a predefined pattern may be detected in different ways such as for example by detecting local maximum and selecting a region of consecutive epochs comprising a predefined number of local maximum or by applying a threshold and selecting only regions comprising at least two consecutive values $h_i$ higher than the threshold or any other way know by the man skilled in the art. In a preferred embodiment, the values of the average vector $V_A$ are binary classified using a predefined threshold generating a binary vector, for example, a binary vector composed of 0 and 1.

According to one embodiment, the predefined threshold is a value below which a predefined percentage of the elements of the average vector $V_A$ falls. The predefined percentage may range between 90 and 99.9 percent. In a preferred embodiment, the threshold is set to a value below which 98 percent of the elements of the average vector falls. The choice of the predefined value directly influences the specificity and the sensitivity of the detection (i.e. the number of false positive detection and the recall rate). According to one embodiment, the detection of predefined patterns is performed on said binary vector. A pattern may be the presence of 2 consecutive equal values in the binary vector; this implies the selection of pathological brain activity lasting at least double the duration of an epoch. This approach as the advantage of removing the noisy events that have been misclassified as pathological brain activity.

According to one embodiment, the method of the present invention comprises a final step of generating an indicator of brain activity Idx of the subject when detecting the predefined pattern. Said indicator of brain activity Idx, may be a binary indicator reporting the presence or absence of pathological brain activity in the acquired electroencephalographic epochs. According to one embodiment, the indicator of brain activity Idx is communicated to a user or a member of a health staff.

Examples of neurological disorders associated with the presence of pathological brain activity in the electroencephalographic signal that can be detected and associated to an indicator by the present method include but are not limited to all of epileptic conditions.

According one embodiment of the present invention, the brain activities that may be detected arise from an epileptic condition.

The ILAE (International League Against Epilepsy) has published in 2010 a revised classification of epileptic conditions (Berg et al, Epilepsia, 51(4):676-685, which is herein incorporated by reference). According to said classification, epileptic conditions may be classified according to the seizure type (generalized seizures, focal seizures, or spasms), etiology (genetic [including idiopathic], structural/metabolic [or symptomatic], or unknown cause [or cryptogenic]), age at onset, cognitive and developmental antecedents and consequences, motor and sensory examinations, EEG features, provoking or triggering factors, and/or patterns of seizure occurrence with respect to sleep.

Examples of epileptic conditions include, but are not limited to, epileptic encephalopathies, early infantile epileptic encephalopathies (EIEEs), Dravet syndrome, benign familial neonatal epilepsy (BFNE), early myoclonic encephalopathy (EME), Ohtahara syndrome, West syndrome, Myoclonic epilepsy in infancy (MEI), benign infantile epilepsy, benign familial infantile epilepsy, myoclonic encephalopathy in non-progressive disorders, febrile seizures plus (FS+), Panayiotopoulos syndrome, epilepsy with myoclonic atonic seizures, benign epilepsy with centrotemporal spikes (BECTS), autosomal-dominant nocturnal frontal lobe epilepsy (ADNFLE), late onset childhood occipital epilepsy, epilepsy with myoclonic absences, Lennox-Gastaut syndrome, epileptic encephalopathy with continuous spike-and-wave during sleep (CSWS), Landau-Kleffner syndrome (LKS), childhood absence epilepsy (CAE), juvenile absence epilepsy (JAE), juvenile myoclonic epilepsy (JME), epilepsy with generalized tonic-clonic seizures alone, progressive myoclonus epilepsies (PME), autosomal dominant epilepsy with auditory features (ADEAF), familial and sporadic epileptic condition, lesional and non-lesional epileptic condition, other familial temporal lobe epilepsies (FTLE) (such as, for example, mesial form of FTLE, familial mesial temporal lobe epilepsy (FMTLE) or familial lateral temporal lobe epilepsy (FLTLE), familial partial epilepsy with variable foci (FPEVF), benign familial partial epilepsies of childhood, reflex epilepsies, mesial temporal lobe epilepsy with hippocampal sclerosis (MTLE with HS), temporal lobe epilepsy, idiopathic generalized epilepsy (IGE), Rasmussen syndrome, gelastic seizures with hypothalamic hamartoma, hemiconvulsion-hemiplegia-epilepsy, neurocutaneous 20 syndromes (tuberous sclerosis complex, Sturge-Weber and the like), epilepsies attributed to malformations of cortical development, tumor, infection or trauma, benign neonatal seizures (BNS), febrile seizures (FS), generalized epilepsy with febrile seizures plus (GEFS+) and epileptic conditions including specific syndromes such as ADNFLE, FTLE, FFEVF, rolandic epilepsies and malignant migrating partial seizures of infancy.

In one embodiment of the present invention, the epileptic condition is generalized epilepsy.

The present invention further relates to a computer program product for calculating an indicator associated to a brain activity of a subject. Said computer program product comprises instructions which, when the computer program is executed by a computer, cause the computer to carry out the steps of the method according to the embodiment described above Computer program code for carrying out operations for aspects of the present invention may be written in any combination of one or more programming languages, including an object oriented programming language such as Java, Python, Ruby, PHP, C++ or the like and conventional procedural programming languages, such as the "C" programming language or similar programming languages. The computer program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

The present invention further relates to a computer-readable storage medium comprising instructions which, when the program is executed by a computer, cause the computer to carry out the carry out the steps of the method according to the embodiment described hereabove.

The computer-readable medium may be a tangible computer readable storage medium storing the computer readable program code. Any combination of one or more computer readable storage media may be utilized. A computer readable storage medium may be, for example, but not limited to, an electronic, magnetic, optical, electromagnetic, infrared, or semiconductor system, apparatus, or device, or any suitable combination of the foregoing.

More specific examples of the computer-readable medium may include but are not limited to a portable computer diskette, a hard disk, a random access memory (RAM), a read-only memory (ROM), an erasable programmable read-only memory (EPROM or Flash memory), a portable compact disc read-only memory (CD-ROM), a digital versatile disc (DVD), a Blu-Ray Disc (BD), an optical storage device, a magnetic storage device, a holographic storage medium, a micromechanical storage device, or any suitable combination of the foregoing. In the context of this document, a computer readable storage medium may be any tangible medium that can contain, and/or store computer readable program code for use by and/or in connection with an instruction execution system, apparatus, or device.

The computer program code may also be loaded onto a computer, other programmable data processing module such as a tablet or phone, or other devices to cause a series of operational steps to be performed on the computer, other programmable apparatus or other devices to produce a computer implemented process such that the program code which execute on the computer or other programmable apparatus provide processes for implementing the steps specified in the flowchart diagram blocks.

Figure 4:
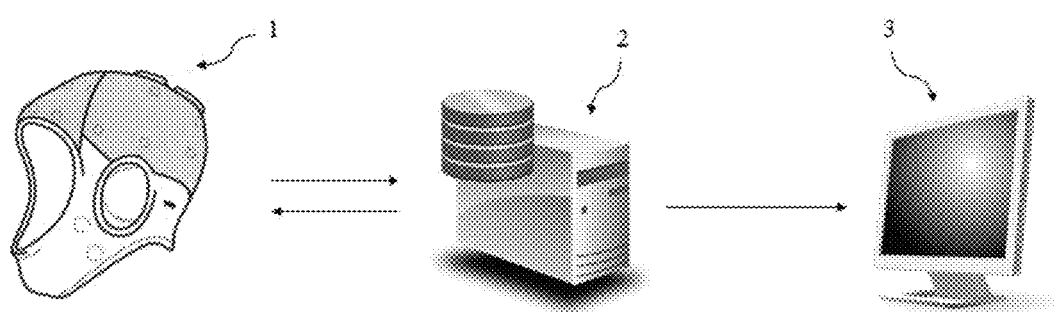
FIG. 4 shows a schematic representation of the components and interaction between components comprised in the system according to one embodiment of present invention.

Another aspect of the present invention, illustrated in FIG. 4, relates to a system for calculating an indicator associated to a brain activity of a subject, the system comprising:
acquisition module 1 for acquiring at least an epoch of electroencephalographic signal ES of a subject from a plurality of electrodes;
a data processing module 2 comprising means for carrying out the steps of the method according to the embodiment in the description hereabove.

According to one embodiment, the acquisition module 1 comprises any means known by one skilled in the art enabling acquisition (i.e. capture, record and/or transmission) of electroencephalographic signals as defined in the present invention, preferably electrodes or headset as explained in the description hereabove. According to one embodiment, the acquisition module comprises an amplifier unit for magnifying and/or converting the electroencephalographic signals from analog to digital format. According to an alternative embodiment, the acquisition module 1 is configured to receive as input a EEG signal previously acquired by an acquisition device other than the system of the present invention.

According to one embodiment, the data processing module 2 is a dedicated circuitry or a general purpose computer, configured for receiving the data and executing the operations described in the embodiment described above. According to one embodiment, the data processing module comprises a processor and a computer program. The processor receives digitalized electroencephalographic signals and processes the digitalized electroencephalographic signals under the instructions of the computer program to compute the indicator Idx. According to one embodiment, the data processing module comprises a network connection enabling remote implementation of the method according to the present invention, for example, in a "cloud". According to one embodiment, electroencephalographic signals are wirelessly communicated to the data processing module.

According to one embodiment, the system further comprises an output generator 3 for reporting the indicator of the brain activity Idx. According to one embodiment, the output generator wirelessly receives the indicator of the brain activity from the data processing module 2.

According to one embodiment, the output generator 3 comprises any means for reporting an indicator of the brain activity. According to one embodiment, the indicator of the brain activity is reported using visual means, auditory means, olfactory means, tactile means (e.g. vibratory or haptic feedback) and/or gustatory means. Preferably, the indicator of the brain activity is reported using a display such as lights; LEDs; a screen; a smartphone, a computer monitor or a television; or a head-mounted display.

While various embodiments have been described and illustrated, the detailed description is not to be construed as being limited hereto. Various modifications can be made to the embodiments by those skilled in the art without departing from the true spirit and scope of the disclosure as defined by the claims.

EXAMPLES

The present invention is further illustrated by the following examples.

Example 1

Materials and Methods
Material
The method according to the present invention was used to detect pathological brain activity in 23 subjects. Said 23 subjects present epilepsy, for which seizures are a characteristic pathological brain activity.

The pre-recorded scalp electroencephalographic signals for those 23 patients were obtained from CHB-MIT Scalp EEG Database, comprising recordings of scalp electroencephalograms of pediatric patients collected at the Children's Hospital of Boston-Massachusetts Institute of Technology. Said electroencephalographic signals were recorded with the international 10-20 system mounted as bipolar, using the following 21 channels: FP1-F7, F7-T7, T7-P7, P7-O1, FP1-F3, F3-C3, C3-P3, P3-O1, FP2-F4, F4-C4, C4-P4, P4-O2, FP2-F8, F8-T8, T8-P8, P8-O2, FZ-CZ, CZ-PZ, T7-FT9, FT9-FT10 and FT10-T8.

The clinical and demographic details of the subjects are specified in the Table 1 below:

TABLE 1

| Patient | Gender | Age | training set (by patients) |
|---|---|---|---|
| 1 | F | 11 | 2-11 |
| 2 | M | 11 | 1 and 3-11 |
| 3 | F | 14 | 1-2 and 4-11 |
| 4 | M | 22 | 1-3 and 5-11 |
| 5 | F | 7 | 1-4 and 6-11 |
| 6 | F | 1.5 | 1-5 and 7-11 |
| 7 | F | 14.5 | 1-6 and 8-11 |
| 8 | M | 3.5 | 1-7 and 9-11 |
| 9 | F | 10 | 1-8 and 10-11 |
| 10 | M | 3 | 1-9 and 11 |
| 11 | F | 12 | 2-11 |
| 12 | F | 2 | 2-11 |
| 13 | F | 3 | 2-11 |
| 14 | F | 9 | 2-11 |
| 15 | M | 16 | 2-11 |
| 16 | F | 7 | 2-11 |
| 17 | F | 12 | 2-11 |
| 18 | F | 18 | 2-11 |
| 19 | F | 19 | 2-11 |
| 20 | F | 6 | 2-11 |
| 21 | F | 13 | 2-11 |
| 22 | F | 9 | 2-11 |
| 23 | F | 6 | 2-11 |

The pre-recorded scalp electroencephalographic signal of subject 12 to 24 presents one or more missing channels. In these cases, in the following example, the number of channels N will refer to the effecting number of channels recorded for a subject.

Methods
For each subject, the 1 hour recordings of each electroencephalographic channel were resampled with a sampling frequency of 256 Hz and segmented into non-overlapping 2 second epochs.

For each segmented epoch of each subject was generated an input matrix $M_{in}$ of said electroencephalographic signals, having dimension (N×512), where 512 is the product of the sampling frequency (i.e. 256 Hz) for the duration of one epoch (i.e. 2 seconds).

The discriminative regular autoencoder was trained multiple times using multiple different training dataset, providing multiple trained autoencoders. Data recorded from subjects 12 to 24 are not used to compose training datasets due the missing channels in the electroencephalographic recordings. In order to evaluate efficiency of the method on each of the subject 12 to 24, the discriminative regular autoencoder was trained on a training dataset comprising the input matrix $M_{in}$ of each epoch from the subjects 2 to 11. In order to evaluate efficiency of the method on the $i^{th}$ subject, for i comprised between 2 and 11, the discriminative regular auto-encoder was trained on a training dataset comprising the input matrix $M_{in}$ of each epoch from the subjects 1 to 11, except the $i^{th}$ subject.

The method of the present invention was finally implemented for each of the electroencephalographic recordings using the appropriate trained autoencoder. The method of the present invention using the discriminative regular autoencoder trained as described above produce an indicator of brain activity associated to epileptic seizures.

For each subject recording, it was counted the number of true positive detections as the times that a seizure was truly detected (i.e. associated to the indicator of seizure) and number of false positive detections as the number of times that a physiological brain activity was wrongly associated to the indicator of seizure. The sensitivity, also called recall rate, is calculated as the ratio between the true positive counts and the sum of true positive counts and false negative counts.

Results

The average recall rate is equal to 64% with a standard deviation of 0.36. The large value of the standard deviation is due to the large age difference between the subject. Indeed, brain activity patterns significantly variates with the ages of children therefore an autoencoder trained on a training dataset comprising only subject of age comprised between 3 and 22 years appears to be unsuitable to detect brain activity indicators in a child of 1.5 years as shown from the recall rate results in Table 2. However, for subject of an age more represented in the training dataset it could be observed a recall rate of 100%, as for subjects 1, 5, 7, 9, 19, 22, 23 and 24.

TABLE 2

| Patient | NB of seizure records | Age | Sex | Fp_per_hour | Recall |
|---|---|---|---|---|---|
| 1 | 7 | 11 | F | 0.15055 | 100% |
| 2 | 2 | 11 | M | 0.79017 | 50% |
| 3 | 7 | 14 | F | 0.85762 | 71% |
| 4 | 3 | 22 | M | 0.46931 | 50% |
| 5 | 5 | 7 | F | 0.20011 | 100% |
| 6 | 7 | 1.5 | F | 1.31324 | 0% |
| 7 | 3 | 14.5 | F | 0.55330 | 100% |
| 8 | 5 | 3.5 | M | 0.40022 | 80% |
| 9 | 3 | 10 | F | 0.93929 | 100% |
| 10 | 7 | 3 | M | 0.64219 | 86% |
| 11 | 3 | 12 | F | 0.71613 | 67% |
| 12 | 10 | 2 | F | 1.34321 | 26% |
| 13 | 8 | 3 | F | 1.25069 | 8% |
| 14 | 7 | 9 | F | 2.14404 | 0% |
| 15 | 14 | 16 | M | 1.49976 | 25% |
| 16 | 6 | 7 | F | 1.50083 | 10% |
| 17 | 3 | 12 | F | 0.67000 | 67% |
| 18 | 6 | 18 | F | 1.24371 | 67% |
| 19 | 3 | 19 | F | 0.34155 | 100% |
| 20 | 6 | 6 | F | 0.35953 | 100% |
| 21 | 4 | 13 | F | 0.78363 | 50% |
| 22 | 3 | 9 | F | 0.00000 | 100% |
| 23 | 3 | 6 | F | 0.78144 | 100% |
| 24 | 12 | — | — | 0.75041 | 100% |

The invention claimed is:

1. A system for calculating an indicator associated to a determined brain activity of a subject, the system comprising:
   acquisition module configured to acquire at least an epoch of electroencephalographic signal of a subject from a plurality of electrodes; and
   a data processing module configured to carry out the steps of:
   calculating an average vector according to the following steps:
   receiving at least an epoch of electroencephalographic signals of a subject acquired from a plurality of electrodes;
   generating an input matrix (n×m) of said electroencephalographic signals, having the n dimension equal to N, number of channels of the electroencephalographic recording; said input matrix being provided as input to an auto-encoder neural network;
   generating a reconstructed output matrix using the auto-encoder;
   generating a loss values vector by linear combination of the input matrix and output matrix, wherein each element of the loss value vector is associated to a channel; and
   calculating the average value of the elements of the loss values vector;
   said calculating step being repeated multiple times to generate an average vector comprising the average values obtained for each consecutive electroencephalographic epoch;
   detecting the presence of at least a predefined pattern in the consecutive average values of the average vector; and
   generating an indicator of brain activity of the subject when detecting the predefined pattern, the indicator being representative of the determined brain activity, an output generator for reporting the indicator of the brain activity.

2. The system according to claim 1, wherein the autoencoder is trained with a training dataset comprising a plurality of predefined electroencephalographic signals over a predefined time period.

3. The system according to claim 1, wherein the auto-encoder comprises at least two hidden layers of neurons.

4. The system according to claim 1, wherein the data processing module is further configured to carry out a step of binary classifying the elements of the average vector according to a predefined threshold.

5. The system according to claim 4, wherein the predefined threshold is a value below which 98 percent of the elements of the average vector falls.

6. The system according to claim 1, wherein each average value of the elements of the loss values vector is calculated with a harmonic mean.

7. The system according to claim 1, wherein the predefined pattern is configured to detect two consecutive average values of the average vector comprised in a predefined range of values.

8. The system according to claim 1, wherein electroencephalographic signal is acquired at a sampling rate of at least 256 Hz.

9. The system according to claim 1, wherein the m dimension of the input matrix ($M_{in}$) is defined according to the sampling rate and the epoch time window.

10. The system according to claim 1, further comprising an output generator for reporting the indicator of the brain activity.

11. A method for calculating an indicator associated to a determined brain activity of a subject, said method comprising the following steps:
calculating an average vector according to the following steps:
receiving at least an epoch of electroencephalographic signals of a subject acquired from a plurality of electrodes;
generating an input matrix (n×m) of said electroencephalographic signals, having the n dimension equal to N, number of channels of the electroencephalographic recording; said input matrix being provided an input to for an auto-encoder neural network;
generating a reconstructed output matrix using the auto-encoder;
generating a loss values vector by linear combination of the input matrix and output matrix, wherein each element of the loss value vector is associated to a channel; and
calculating the average value of the elements of the loss values vector;
said calculating step being repeated multiple times to generate an average vector comprising the average values obtained for each consecutive electroencephalographic epoch;
detecting the presence of at least a predefined pattern in the consecutive average values of the average vector; and
generating an indicator of brain activity of the subject when detecting the predefined
pattern the indicator being representative of the determined brain activity, reporting the indicator of the brain activity.

12. The method according to claim 11, wherein the autoencoder is trained with a training dataset comprising a plurality of predefined electroencephalographic signals over a predefined time period.

13. The method according to claim 11, wherein the auto-encoder comprises at least two hidden layers of neurons.

14. The method according to claim 11, further comprising a step of binary classifying the elements of the average vector according to a predefined threshold.

15. The method according to claim 14, wherein the predefined threshold is a value below which 98 percent of the elements of the average vector falls.

16. The method according to claim 11, wherein each average value of the elements of the loss values vector is calculated with a harmonic mean.

17. The method according to claim 11, wherein the predefined pattern is configured to detect two consecutive average values of the average vector comprised in a predefined range of values.

18. The method according to claim 11, wherein electroencephalographic signal is acquired at a sampling rate of at least 256 Hz.

19. The method according to claim 11, wherein the m dimension of the input matrix is defined according to the sampling rate and the epoch time window.

20. A computer program product for calculating an indicator associated to a determined brain activity of a subject, the computer program product comprising instructions which, when the program is executed by a computer, cause the computer to carry out the steps of the method according to claim 11.

21. A computer-readable storage medium comprising instructions which, when the program is executed by a computer, cause the computer to carry out the steps of the method according to claim 11.

* * * * *